United States Patent [19]
DeWall

[11] Patent Number: 5,007,412
[45] Date of Patent: Apr. 16, 1991

[54] BACK SUPPORT VEST

[76] Inventor: Terry L. DeWall, 6110 N. 100th Plz., Omaha, Nebr. 68134

[21] Appl. No.: 535,686

[22] Filed: Jun. 11, 1990

[51] Int. Cl.$^5$ .............................................. A61F 5/02
[52] U.S. Cl. ................................... 128/78; 128/84 R; 128/379; 128/DIG. 15; 2/44; 2/102
[58] Field of Search .............. 128/78, 75, 84 R, 87 R, 128/96.1, 99.1, 100.1, 102.1, 106.1, 107.1, 379 X, 384, DIG. 15 X; 2/44 X, 92, 102 X

[56] References Cited

U.S. PATENT DOCUMENTS

| | | | |
|---|---|---|---|
| 2,664,888 | 1/1954 | Sutter | 2/44 X |
| 4,022,197 | 5/1977 | Castiglia | 128/96.1 X |
| 4,475,543 | 10/1984 | Brooks et al. | 128/78 |
| 4,820,221 | 4/1989 | Aubrey | 128/78 X |

Primary Examiner—Robert Bahr
Assistant Examiner—Jennifer L. Doyle
Attorney, Agent, or Firm—Henderson & Sturm

[57] ABSTRACT

A back support vest including a lower back supporting section formed of elastic material that encircles the body in the lumbar and lumbosacral region, an upper back supporting section formed of non-elastic material that encircles the body in the thoracolumbar and thoracic region, and shoulder straps that join the front and rear lateral portions of the upper section. The vest also includes a reinforced section that spans the lower and upper sections centering on the dorsolumbar region. The elastic material of the lower section keeps the reinforced section in tension to provide effective support. Additional support is provided by pockets that releasably attach to the rear of the vest and are adapted to hold additional back support devices such as pillows, inflatables and molded spinal orthoses.

8 Claims, 4 Drawing Sheets

BACK SUPPORT VEST

TECHNICAL FIELD

This invention relates to a back support vest, and more particularly to a vest that provides support of the entire back area from the thoracic to the lumbosacral region.

BACKGROUND ART

Eight out of ten Americans experience a painful back episode at some time during their lives. One hundred million Americans have serious back problems, and over one-quarter million have back surgery each year.

Many devices are known that provide support to specific regions of the back. However, no previously known device provides effective support to the entire back area to maintain the normal curvature of the spine while engaging in various physical activities.

Those concerned with these and other problems recognize the need for an improved back support vest.

DISCLOSURE OF THE INVENTION

The present invention provides a back support vest including a lower back supporting section formed of elastic material that encircles the body in the lumbar and lumbosacral region, an upper back supporting section formed of non-elastic material that encircles the body in the thoracolumbar and thoracic region, and shoulder straps that join the front and rear lateral portions of the upper section. The vest also includes a reinforced section that spans the lower and upper sections centering on the dorsolumbar region. The elastic material of the lower sections keeps the reinforced section in the tension to provide effective support. Additional support is provided by pockets that releasbly attach to the rear of the vest and are adapted to hold additional back support devices such as pillows, inflatables and molded spinal orthoses.

An object of the present invention is the provision of an improved back support vest.

Another object is to provide a back support vest that simultaneously supports the entire back, lifts the chest to move the shoulders back to a released position, and maintains the natural curvature of the spine.

A further object of the invention is the provision of a back support support vest that is washable and easy to maintain.

Still another object is to provide a back support vest that is durable.

A still further object of the present invention is the provision of a back support vest that molds to the wearer's body, is cool and comfortable, and can be worn under street clothes without being noticeable.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 2:
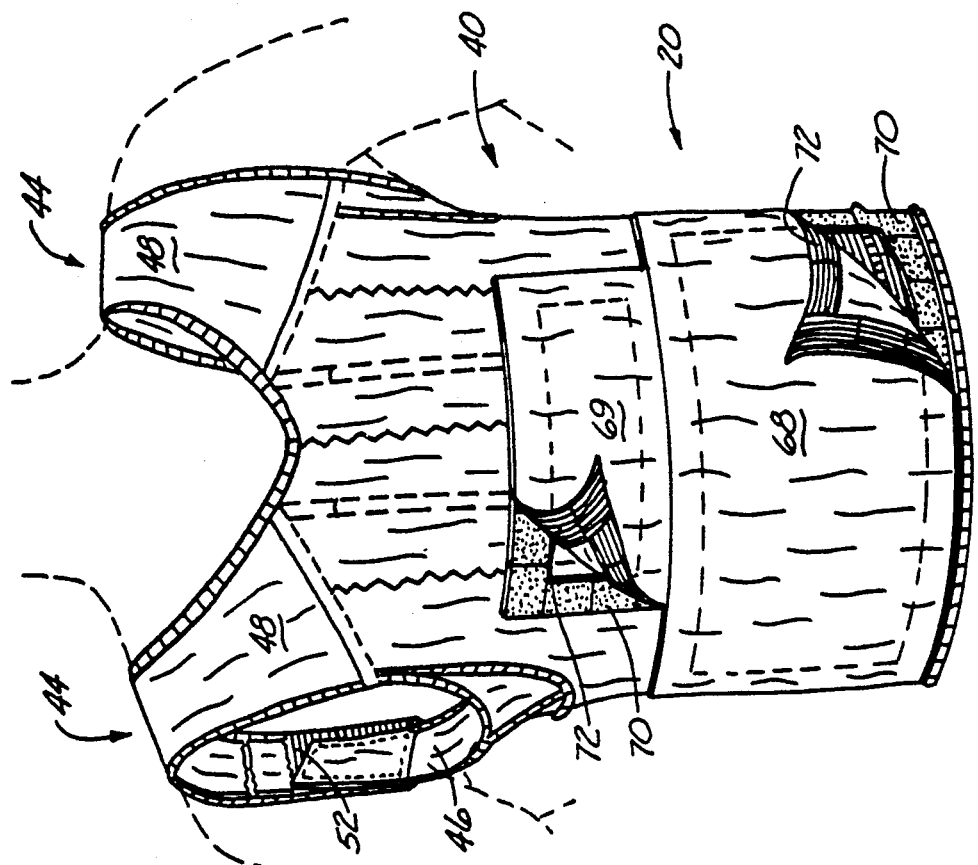
FIG. 2 is a perspective view showing the rear of the vest having the selectively detachable pockets secured by hook and loop strips.
Figure 1:
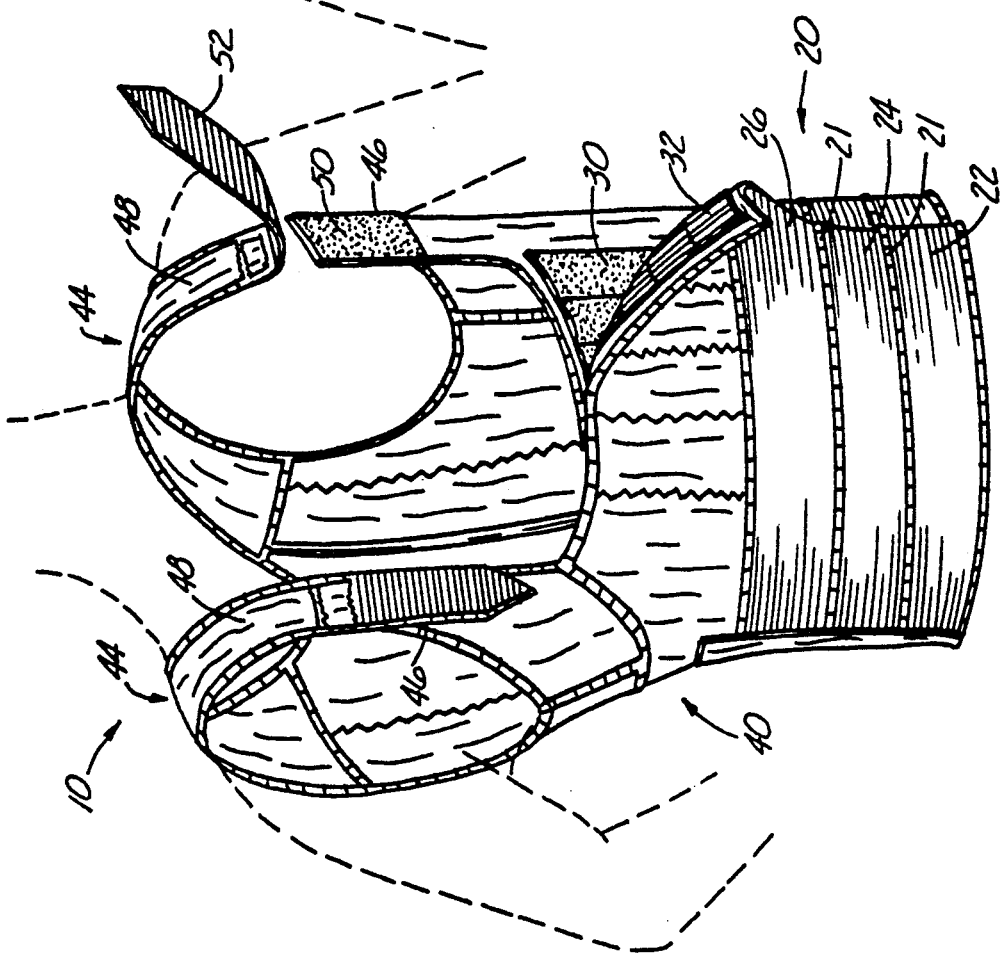
FIG. 1 is a perspective view of the back support vest of the present invention showing the front side having overlapping ends with the hook and loop type fastener to secure the vest in body encircling position, and the adjustable shoulder straps.
Figure 3:
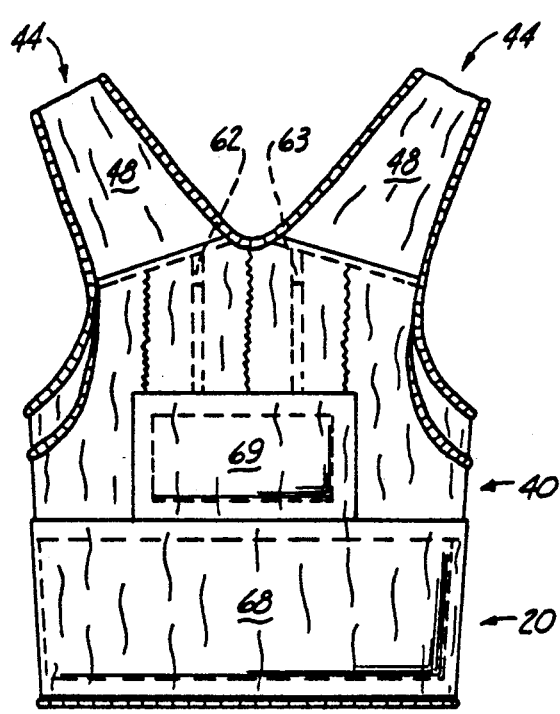
FIG. 3 is a rear elevational view showing the detachable pockets in place.
Figure 4:
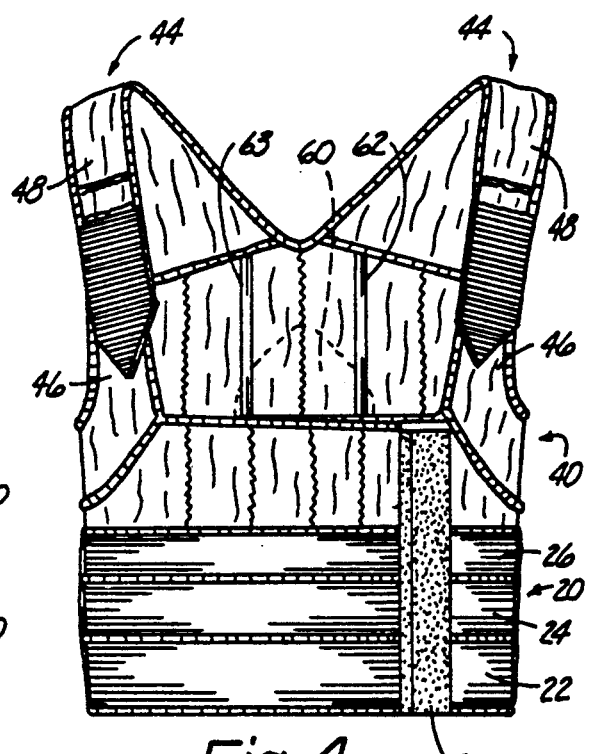
FIG. 4 is a front elevational view.
Figure 6:
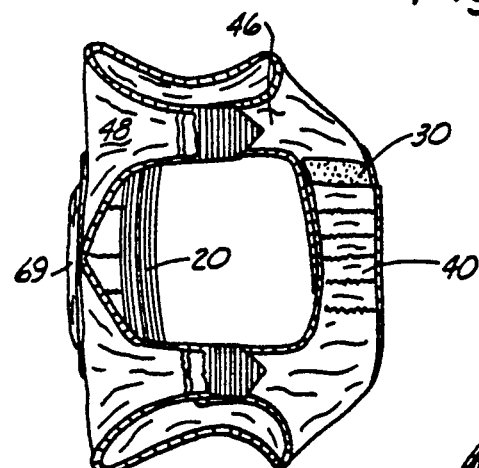
FIG. 6 is a top plan view.
Figure 5:
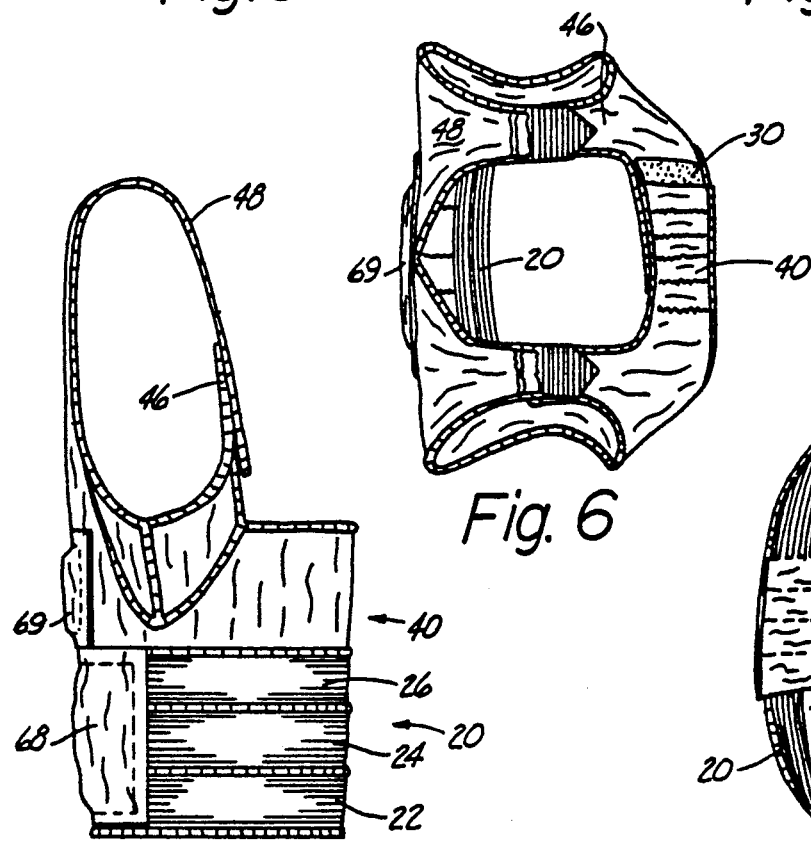
FIG. 5 is a side elevational view.
Figure 7:
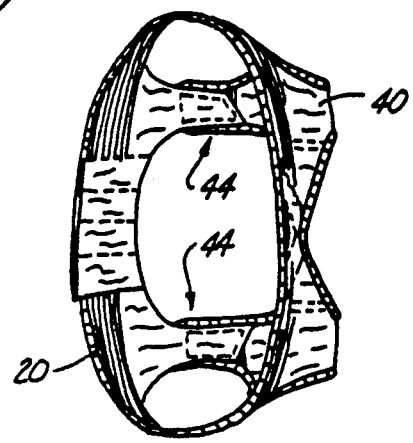
FIG. 7 is a bottom plan view.

Referring now to the drawings, wherein like reference numerals designate identical or corresponding parts throughout the several views, FIG. 1 shows the back support vest (10) of the present invention. The vest (10) includes a lower back supporting section (20) made of parallel panels (22, 24, 26) of elastic material joined by stitching (21). The lower panel (20) encircles the lumbar and lumbosacral region of the human body. An upper back supporting section (40) is formed of non-elastic material attached to the lower section (20). The upper section (40) encircles the body in the thoracolumbar and thoracic region. The rear of the upper section (40) extends up to the neck area while the front extends only over the abdomen up to the chest area. The front of the lower section (20) and the upper section (40) having overlapping ends that carry Velcro-type fasteners (30, 32) secured to the entire opposing surfaces of the overlapping ends to provide a large area of contact which results in a secure attachment and reliable support. A pair of selectively, adjustable shoulder straps (44) are formed by joining extensions (46, 48) by hook and loop type fasteners (50, 52).

Figure 8:
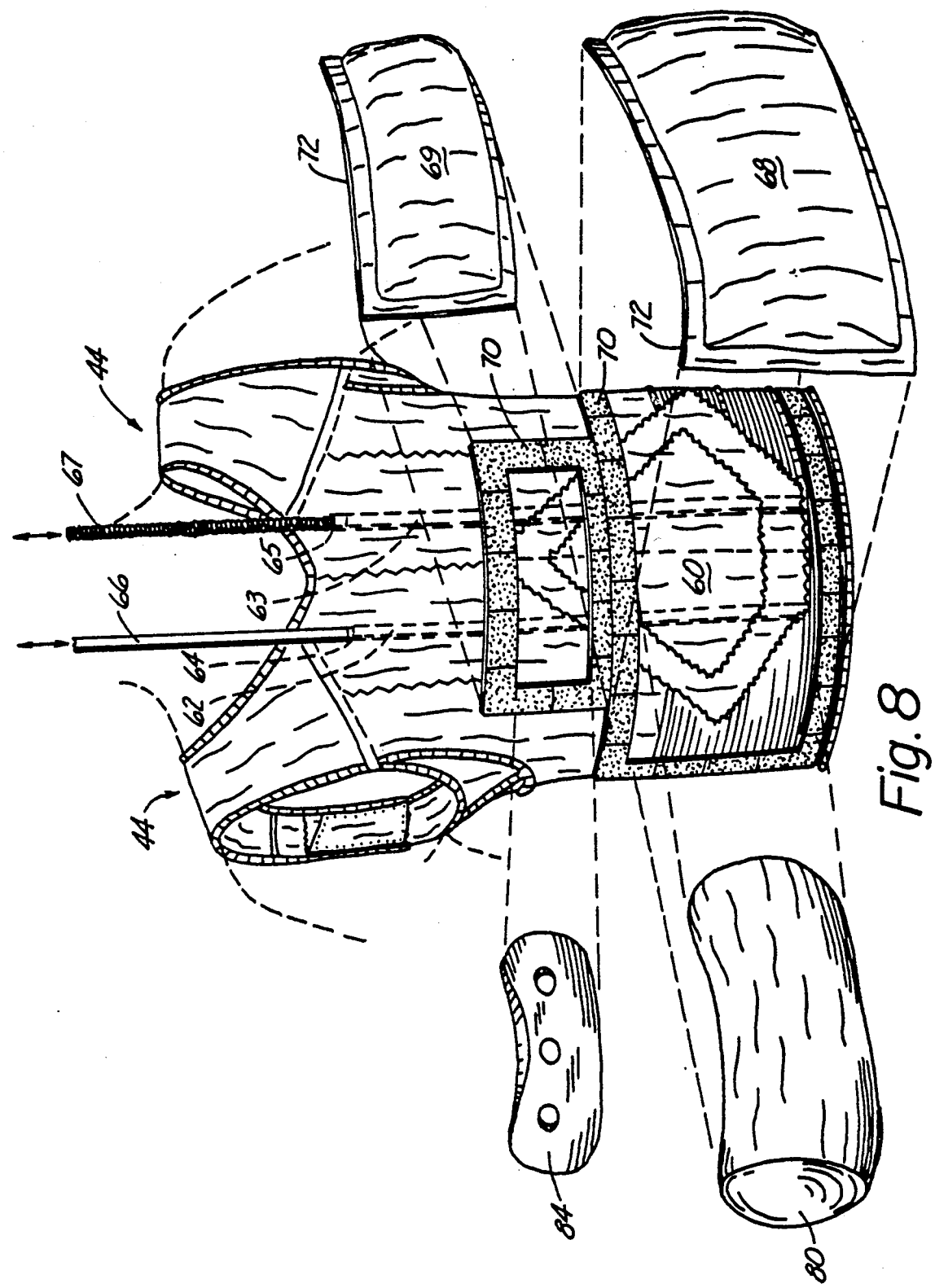
FIG. 8 is an exploded perspective view illustrating the positioning of support devices in the detachable pockets.
Figure 9:
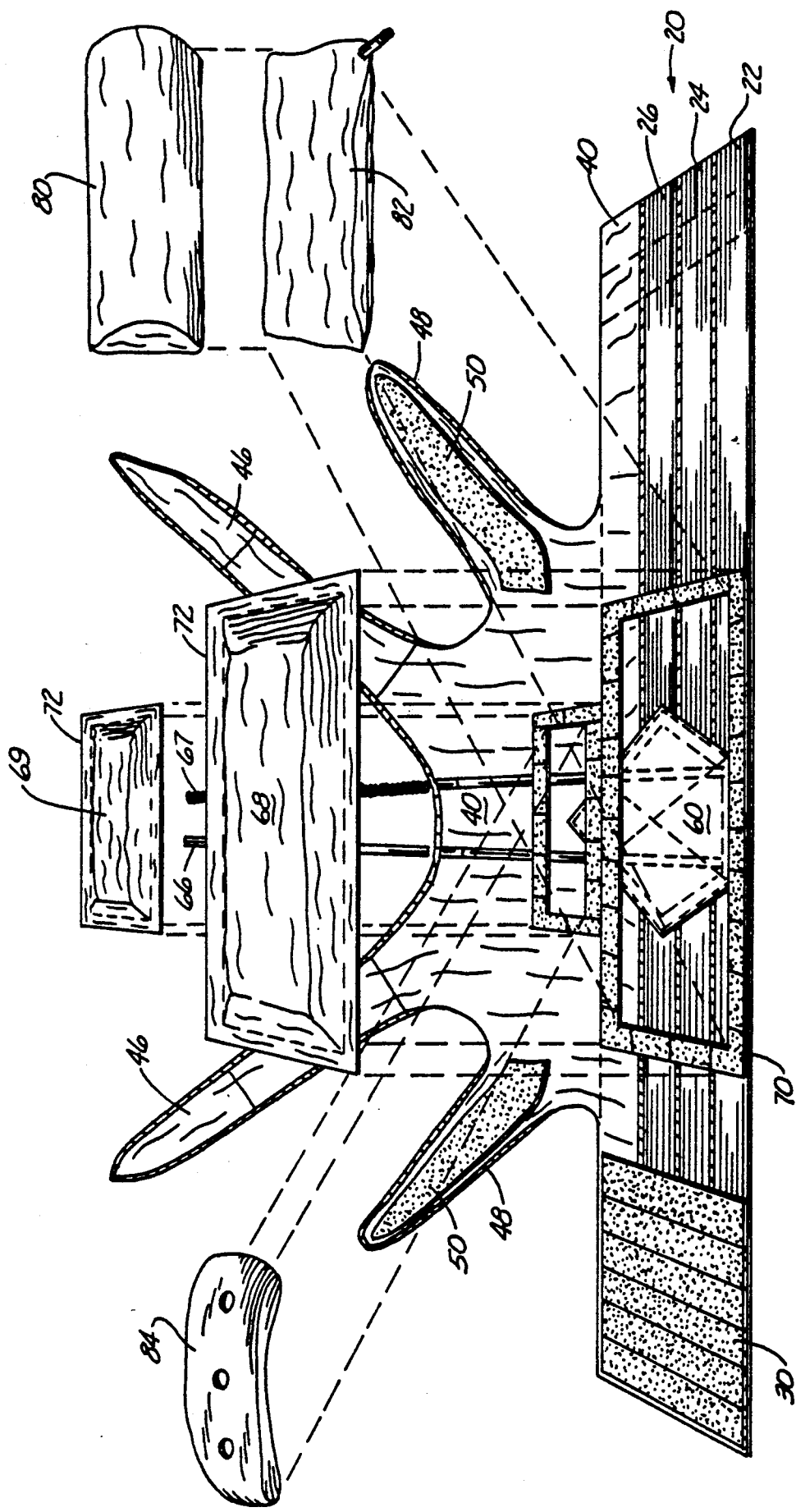
FIG. 9 is an exploded perspective view illustrating the rear of the vest in an open layed-out configuration, and showing the orientation of the supporting devices in the detachable pockets.

As best shown in FIGS. 8 and 9, a reinforced section (60) is attached by stitching to the rear of the vest (10). The reinforced section (60) is formed of a triple layer of non-elastic material that spans the lower section (20) and the upper section (40), and is centered on and extends across the dorsolumbar region. The elastic material of the lower section (20) keeps the reinforced section (60) in tension to provide effective support to the dorsolumbar region when the vest (10) is worn. A pair of sleeves (62, 63), including slit openings (64, 65) are formed in the rear of the vest (10) to receive vertical supports (66, 67) formed of bone, wire mesh, or other suitable material.

The rear of the vest (10) carries a detachable pocket (68) and an auxiliary pocket (69) attached by hook and loop strips (70, 72) as illustrated in FIGS. 8 and 9. The pockets (68, 69) are adapted to selectively receive a number of supporting devices such as pillows (80), inflatables (82), and molded spinal orthoses (84).

The vest (10) may be made in a number of standard sizes, e.g., Small, Medium, Large, Extra Large. Also, the overlapping ends and the shoulder straps can be selectively positioned to provide a proper fit for each individual user.

When in use, the vest (10) simultaneously supports the entire back, lifts the chest, and maintains the natural curvature of the spine while the user engages in various physical activities.

Thus, it can be seen that at least all of the stated objectives have been achieved.

Obviously, many modifications and variations of the present invention are possible in light of the above teachings. It is therefore to be understood that, within the scope of the appended claims, the invention may be practised otherwise than as specifically described.

I claim:

1. A back support vest, comprising:
a lower back supporting section including an elastic material disposed to encircle a human body in the lumbar and lumbosacral region
an upper back support section having front and rear lateral portions and including a non-elastic material attached to and extending above said lower section and disposed to encircle the body in the thoracolumbar and thoracic region and a common means for releasably securing the ends of both the upper and lower sections includes overlapping ends attached with a hook and loop type fastener; wherein said fastener extends over the entire opposing surfaces of the overlapping ends of the upper and lower sections;
a pair of shoulder straps disposed to join front and rear lateral portions of the upper section; and,
a reinforced section including multiple layers of non elastic material attached to said vest and disposed to span the lower section and the upper section, said reinforced section being centered on and extending across the dorsolumbar region and extending upwardly therefrom, and,
vertical supports attached to the rear of said vest and disposed to span the lower section and the upper section in spaced parallel relationship to the spine.

2. The back support vest of claim 1 wherein each of said vertical supports is carried in a sleeve formed in the rear of said vest.

3. The back support vest of claim 2 wherein said sleeves include slip openings for selective removal and insertion of said vertical supports.

4. The back support vest of claim 2 further including a pocket attached to the rear of said vest and disposed to extend across the lower section, said pocket being adapted to selectively receive a support device.

5. The back support vest of claim 4 further including an auxiliary pocket attached to the rear of said vest above said pocket and disposed to extend across the upper section, said auxiliary pocket being adapted to selectively receive a support device.

6. The back support vest of claim 5 wherein said supporting device is a molded spinal orthoses.

7. The back support vest of claim 5 wherein said auxiliary pocket is selectively detachable from the rear of said vest.

8. The back support vest of claim 7 wherein said auxiliary pocket is attached with a hook and loop fastener.

* * * * *